United States Patent
Fricker et al.

(10) Patent No.: US 6,527,872 B1
(45) Date of Patent: Mar. 4, 2003

(54) ENVIRONMENTALLY FRIENDLY PERACETIC ACID DECONTAMINATION FORMULA WITH INCREASED PERFORMANCE AND CHEMICAL STABILITY

(75) Inventors: Christopher M. Fricker, Concord, OH (US); Brian C. Wojcieck, Madison, OH (US); Stephanie A. S. Harrington, Mentor, OH (US); Iain F. McVey, Lakewood, OH (US); George E. Grignol, Fairview, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/974,499

(22) Filed: Oct. 10, 2001

Related U.S. Application Data

(63) Continuation of application No. 09/362,841, filed on Jul. 28, 1999, now abandoned.

(51) Int. Cl.[7] .............................. B08B 3/04; C11D 7/02; C11D 7/16; C11D 7/56
(52) U.S. Cl. .......................... 134/42; 134/41; 510/161; 510/372; 510/375; 510/380; 510/382; 510/383; 510/507; 510/512
(58) Field of Search ................................ 510/372, 375, 510/377, 380, 507, 512, 382, 383, 161; 134/41, 42

(56) References Cited

U.S. PATENT DOCUMENTS

| | | |
|---|---|---|
| 4,731,222 A | 3/1988 | Kralovic et al. ............... 422/37 |
| 5,037,623 A | 8/1991 | Schneider et al. ........... 422/292 |
| 5,055,219 A | 10/1991 | Smith .......................... 252/102 |
| 5,077,008 A | 12/1991 | Kralovic et al. ............... 422/37 |
| 5,116,575 A | 5/1992 | Badertscher et al. .......... 422/28 |
| 5,217,698 A | 6/1993 | Siegel et al. ................. 422/295 |
| 5,225,160 A | 7/1993 | Sanford et al. ................ 422/28 |
| 5,287,590 A | 2/1994 | Yonkers et al. ................ 15/321 |
| 5,350,563 A | 9/1994 | Kralovic et al. ............... 422/28 |
| 5,374,369 A | 12/1994 | Angevaare et al. ......... 252/102 |
| 5,439,654 A | 8/1995 | Kochte ........................ 422/292 |
| 5,480,576 A | 1/1996 | Gary et al. .................... 252/95 |
| 5,552,115 A | 9/1996 | Malchesky ................... 422/28 |
| 5,662,866 A | 9/1997 | Siegel et al. .................. 422/29 |
| 5,696,046 A | 12/1997 | Green ......................... 502/161 |
| 5,827,808 A | 10/1998 | Appleby et al. ............. 510/220 |
| 6,083,898 A | 7/2000 | Meixner et al. ............. 510/499 |

Primary Examiner—Gregory Delcotto
(74) Attorney, Agent, or Firm—Fay, Sharpe, Fagan, Minnich & McKee, LLP

(57) ABSTRACT

An environmentally friendly decontaminant solution, which may be disposed of after use without posing significant environmental hazards, is formulated without molybdenum-based corrosion inhibitors and preferably is free of all heavy metals. A zeolite-based buffering system optionally replaces phosphate buffers for maintaining the pH of the decontaminant solution at an appropriate pH for effective antimicrobial decontamination. Molybdenum-free decontaminant solutions containing peracetic acid retain their peracetic acid levels, and thus their antimicrobial effectiveness, for longer periods than comparable solutions formulated with a molybdate corrosion inhibitor.

15 Claims, 8 Drawing Sheets

ENVIRONMENTALLY FRIENDLY PERACETIC ACID DECONTAMINATION FORMULA WITH INCREASED PERFORMANCE AND CHEMICAL STABILITY

This is a continuation of application Ser. No. 09/362,841, filed Jul. 28, 1999, now abandoned.

BACKGROUND OF THE INVENTION

The present invention relates to the decontamination arts. It finds particular application as a composition to be used in conjunction with a liquid or dry sterilizing or disinfecting concentrate to form an environmentally friendly, microbicidally active solution containing peracetic acid with extended stability upon mixing with water and will be described with particular reference thereto. It should be appreciated, however, that the invention is also applicable to other liquid sterilization and disinfection processes where quantities of a decontaminant are to be used.

Disinfection connotes the absence of pathogenic life forms. Sterilization connotes the absence of all life forms, whether pathogenic or not. The term decontamination is used herein to connote sterilization, disinfection or other anti-microbial treatments.

Until recently, medical equipment and instruments were often decontaminated in a steam autoclave. Autoclaves kill life forms with a combination of high temperature and pressure. However, steam autoclaves have several drawbacks. The pressure vessels are often bulky and heavy. The high temperature and pressures used tend to curtail the useful life of endoscopes, rubber and plastic devices, lenses, and portions of devices made of polymeric materials and the like. Moreover, a typical autoclave decontaminating and cool down cycle is sufficiently long that multiple sets of the medical instruments are commonly required.

Liquid decontamination systems have been developed for equipment which can not withstand the high temperatures of steam decontamination. Traditionally, a technician mixed a liquid disinfectant or sterilant composition immediately prior to use and manually immersed the items to be decontaminated. More recently, automated decontamination systems have been developed in which a premeasured dose of a decontaminant in solution is circulated through the system. Examples of such systems are disclosed in U.S. Pat. Nos. 4,892,706 and 5,217,698. Items to be decontaminated are inserted into a receiving tray of the system and a cartridge of concentrated decontaminant inserted into a well. As water flows through the system, the decontaminant is diluted and carried to the receiving tray. At the end of a decontamination cycle, the decontaminant solution is disposed of and a fresh cartridge of the concentrated decontaminant is inserted into the system for the next cycle.

The decontaminant for the system may be formed from a liquid concentrate or a powdered composition. U.S. Pat. No. 5,007,008 discloses a liquid concentrate comprising peracetic acid. U.S. Pat. Nos. 5,116,575 and 5,350,563 disclose powdered anti-microbial compositions. The powdered anti-microbial compositions include two components which react in the presence of water to form a strong oxidant. Preferably, acetylsalicylic acid and a perborate, such as sodium perborate, are reacted to form peracetic acid. The powdered components further include surfactants, anti-corrosive materials, chelating agents, and buffers. The anti-corrosive materials inhibit corrosion of brass, copper, aluminum, steel, and other materials commonly found in medical, dental, and surgical instruments. The buffers, particularly phosphates, maintain the pH at around neutral and also act as anti-corrosives.

Liquid concentrates may be aspirated into the automated system from an ampule or capsule, as disclosed in U.S. Pat. No. 5,007,008. Powdered components are preferably stored separately until use. U.S. Pat. No. 5,662,866 to Siegel, et al. discloses a two-compartment cup which holds powdered components.

The present inventors have found that corrosion inhibitors containing heavy metals, such as molybdenum, tend to degrade the peracetic acid in the formulation during the decontamination process, contributing to a loss in effectiveness of the decontaminant solution.

Further, when large quantities of waste decontaminant solution are generated, the presence of some components, such as phosphates and heavy metals, in the waste may increase disposal costs. Environmental regulations often mandate maximum levels of heavy metals in waste waters and solid wastes. In the case of phosphates, the maximum levels have been reduced in recent years due to concerns that the biological oxygen demand of waters into which the wastes are released may become too high to support aquatic life. Sometimes, regulations require precipitation of waste water components.

An environmentally friendly decontaminant composition without phosphates would eliminate costly purification of the waste. Moreover, although phosphates in the waste precipitates can be used as fertilizers, the presence of certain heavy metals with the phosphates makes the precipitates undesirable for such a use. An environmentally friendly decontaminant composition without heavy metals would reduce costly purification of the waste.

The present invention provides for a new and improved decontaminant composition which overcomes the above-referenced problems and others.

SUMMARY OF THE INVENTION

In accordance with one aspect of the present invention, an environmentally-friendly composition which forms an effective decontaminant solution when mixed with an anti-microbial agent and water is provided. The composition includes a buffering system for buffering the pH of the decontaminant solution to a suitable pH for antimicrobial decontamination, the buffering system including at least one buffer selected from the group consisting of phosphates and zeolites and a corrosion inhibitor for inhibiting corrosion of metal components to be contacted by the decontaminant solution, the corrosion inhibitor being free of molybdenum and compounds thereof.

In accordance with another aspect of the present invention, a decontaminant solution with longer effective life is provided. The solution includes an antimicrobial agent and a buffering system which buffers the pH of the decontaminant solution to a suitable pH for antimicrobial decontamination. The buffering system including at least one buffer selected from the group consisting of phosphates and zeolites. The solution also includes a corrosion inhibitor for inhibiting corrosion of metal components to be contacted by the decontaminant solution. The corrosion inhibitor is free of molybdenum.

In accordance with another aspect of the present invention, a method of decontamination is provided. The method includes combining an antimicrobial agent and a composition with water to form a decontaminant solution. The composition includes a buffering system for buffering the pH of the decontaminant solution to a suitable pH for antimicrobial decontamination. The buffering system includes at least one buffer selected from the group consisting of phosphates and zeolites. The composition further includes a corrosion inhibitor for inhibiting corrosion of metal components to be contacted by the decontaminant solution, the corrosion inhibitor being free of molybdenum. The method further includes contacting items to be decontaminated with the solution for sufficient time to substantially antimicrobially decontaminate them.

In accordance with another aspect of the present invention, an environmentally-friendly composition which forms an effective decontaminant solution when mixed with an antimicrobial agent and water is provided. The composition includes a buffering system for buffering the pH of the decontaminant solution to a suitable pH for antimicrobial decontamination. The buffering system includes a zeolite. The composition also includes a corrosion inhibitor for inhibiting corrosion of metal components to be contacted by the decontaminant solution.

One advantage of the present invention is that the composition is environmentally friendly, facilitating disposal.

Another advantage of the present invention is that the composition is suited to formulation in both dry and liquid forms.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

A concentrated decontamination composition A which is environmentally friendly (i.e., is free of molybdenum and compounds thereof or free of phosphates, or both) is mixed with water and an antimicrobial agent B, such as peracetic acid, lithium hypochlorite, or other strong oxidant, to form a decontaminant solution for sterilizing or disinfecting items, such as medical instruments, and the like. The composition A includes components such as buffers for adjusting the pH to an appropriate level for effective decontamination while maintaining device material compatibility, surfactants for improved penetration of the decontaminant solution, chelating agents to ameliorate the effects of hard water, and corrosion inhibitors for protecting the components of the system and items to be decontaminated from corrosion by the antimicrobial agent.

The corrosion inhibitors in the composition A, such as organic corrosion inhibitors, inorganic sulfates, inorganic phosphates (where present), and the like, are preferably free of molybdenum, and, more preferably, free of all heavy metals. Additionally, the buffers used in the composition are preferably free of phosphates. The composition A is suited to use in a variety of decontamination systems.

The term "decontamination" and other terms relating to decontaminating will be used herein to describe sanitizing, sterilization, disinfection, and other antimicrobial treatments which are designed to remove and/or destroy microorganisms contaminating the items. The terms "free" and "substantially free" are used to indicate that the composition or decontaminant solutions contain no more than impurity amounts of the substances specified. For example, a composition or decontaminant solution which is free or substantially free of molybdenum will contain no more than about 0.001% of molybdenum (i.e, $\leq 10$ ppm).

Figure 1:
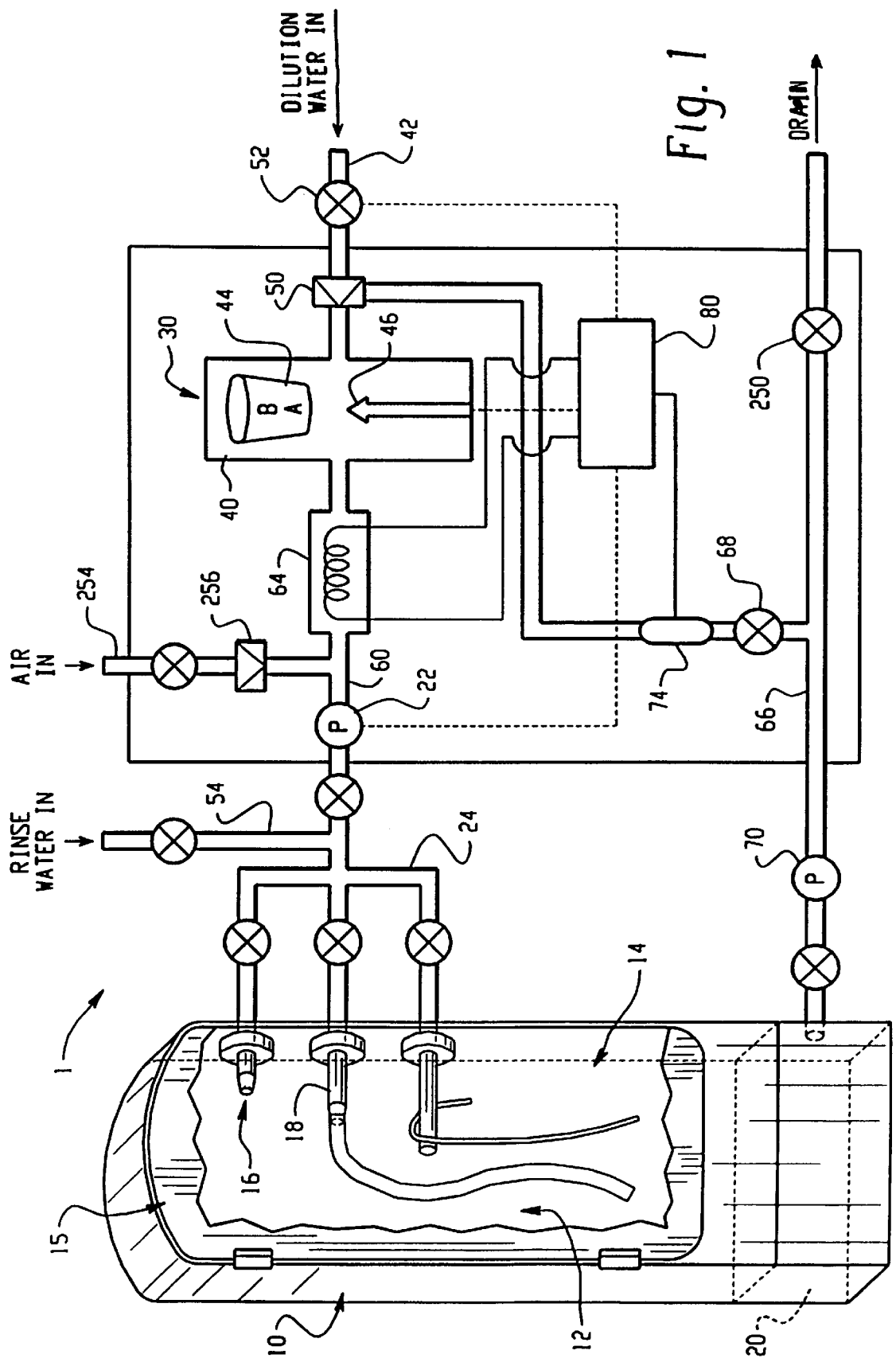
FIG. 1 is a plumbing diagram of a decontamination unit including a cross-sectional view of a reagent cartridge receiving well according to the present invention.

With reference to FIG. 1, an automated liquid system 1 for sanitizing, sterilizing, or disinfecting of items, such as medical, dental, and pharmaceutical devices, and the like, is shown.

The system includes a decontamination cabinet 10 which defines an interior decontamination chamber 12. Items to be sterilized, disinfected, sanitized, or otherwise microbially decontaminated are loaded into the decontamination chamber through an opening in a front wall 14 of the cabinet illustrated as closed by a door 15. Within the chamber, several spray jets or nozzles 16 spray the decontaminant solution over the items. Optionally, in the case of instruments with lumens, or other internal passages, some of the nozzles act as fluid ports 18 which are configured for interconnection with internal passages of the endoscopes and other objects with lumens for supplying decontaminant solution and other liquids to the internal passages.

A collection tank or sump 20 forms the base of the cabinet 10 and receives the sprayed decontaminant solution it drips off the items. A high pressure pump 22 delivers the decontaminant solution under pressure to the nozzles 16 and fluid ports 18 through a fluid distribution system 24.

A source 30 of the decontaminant solution preferably includes a well or chamber 40. The well receives a dose of the antimicrobial agent and the composition A. A water inlet 42 supplies fresh dilution water to the well. The water mixes with the antimicrobial agent B and the composition A in the well to form the decontaminant solution.

Preferably, the antimicrobial agent B and the composition A are supplied in a disposable package or cup 44 which is positioned in the well 40 prior to a decontamination cycle. The cup 44 holds measured doses of the antimicrobial agent B and the composition A. Optionally, a cleaner concentrate C is also contained in the cup for forming a cleaning solution to clean the items prior to antimicrobial decontamination. The cup may include a number of compartments which separately contain the cleaning concentrate C, antimicrobial agent B, and the composition A for separate release into the system. In this way, the items are first cleaned and then microbially decontaminated.

A cup cutter 46, or other suitable opening member, is positioned at the base of the well 40 for opening selected compartments of the cup. The water used for diluting the cleaner concentrate C, antimicrobial agent B, and the composition A may be tap water or treated water, such as distilled water, filtered water, microbe free water, or the like. The quantity of water entering the system is regulated to provide a decontaminant solution of a desired concentration in the decontamination chamber 12. The water is preferably passed through a microporous filter 50 in the water inlet line 42 which filters out particles of dirt and microorganisms. A valve 52 in the water inlet 42 closes when the selected quantity of water has been admitted. The inlet line 42 is optionally used for supplying a rinse water, for rinsing the items after decontamination is complete. Alternatively, as shown in FIG. 1, a separate inlet line 54 is provided to provide a microbe-free rinse water.

A fluid supply line 60 connects the well 40, the pump 22, and the fluid distribution system 24. A heater 64, situated in the fluid supply line 60, heats the decontaminant solution to a preferred temperature for effective decontamination and rinsing. A fluid return line 66 returns the sprayed decontaminant solution from the sump 20. A recirculation valve 68 selectively returns used solution to the fluid supply line 60 and thence to the nozzles 16 and the fluid ports 18. Preferably, a return pump 70 pumps the sprayed decontaminant solution through the return fluid line 66, to be returned to the chamber 12. Alternatively, the return pump is eliminated and the high pressure pump 22 circulates the decontaminant solution. At least a portion of the sprayed decontaminant solution is directed through the well 40 before being returned to the decontamination chamber. This ensures thorough mixing of the cup components with the solution before returning the decontaminant solution to the nozzles 16, 18. Optionally, a detector 74 detects the concentration of one or more antimicrobial agent, peracetic acid in the preferred embodiment, passing through the fluid lines. The detector may be an electrochemical monitoring system or a system employing chemical analysis.

A computer control system 80 controls the operation of the system 1, including the pumps 22, 70, the heater 64, the valves 52, and the like.

Figure 2:
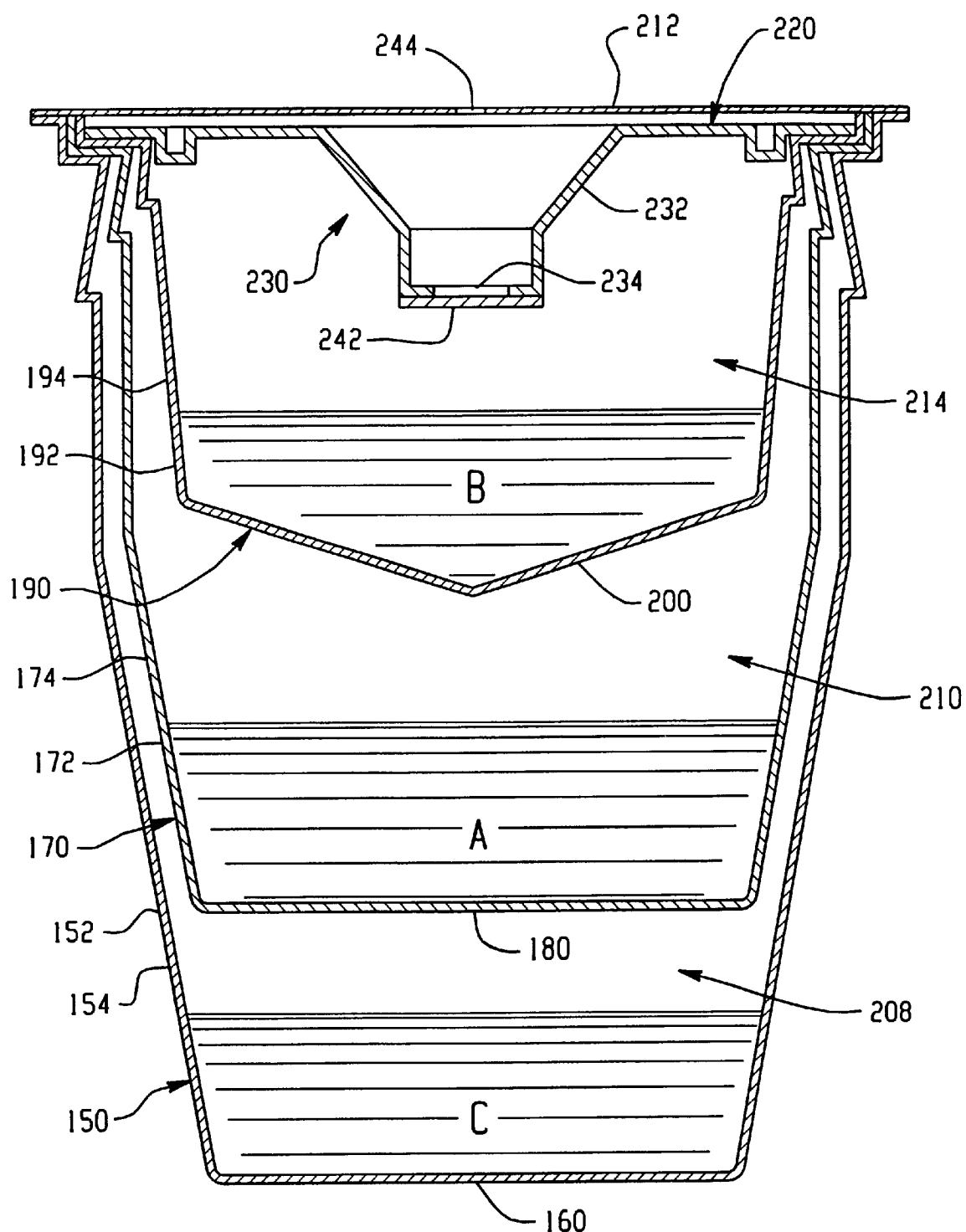
FIG. 2 is a side sectional view of a first preferred embodiment of a three-compartment reagent cartridge according to the present invention.
Figure 3:
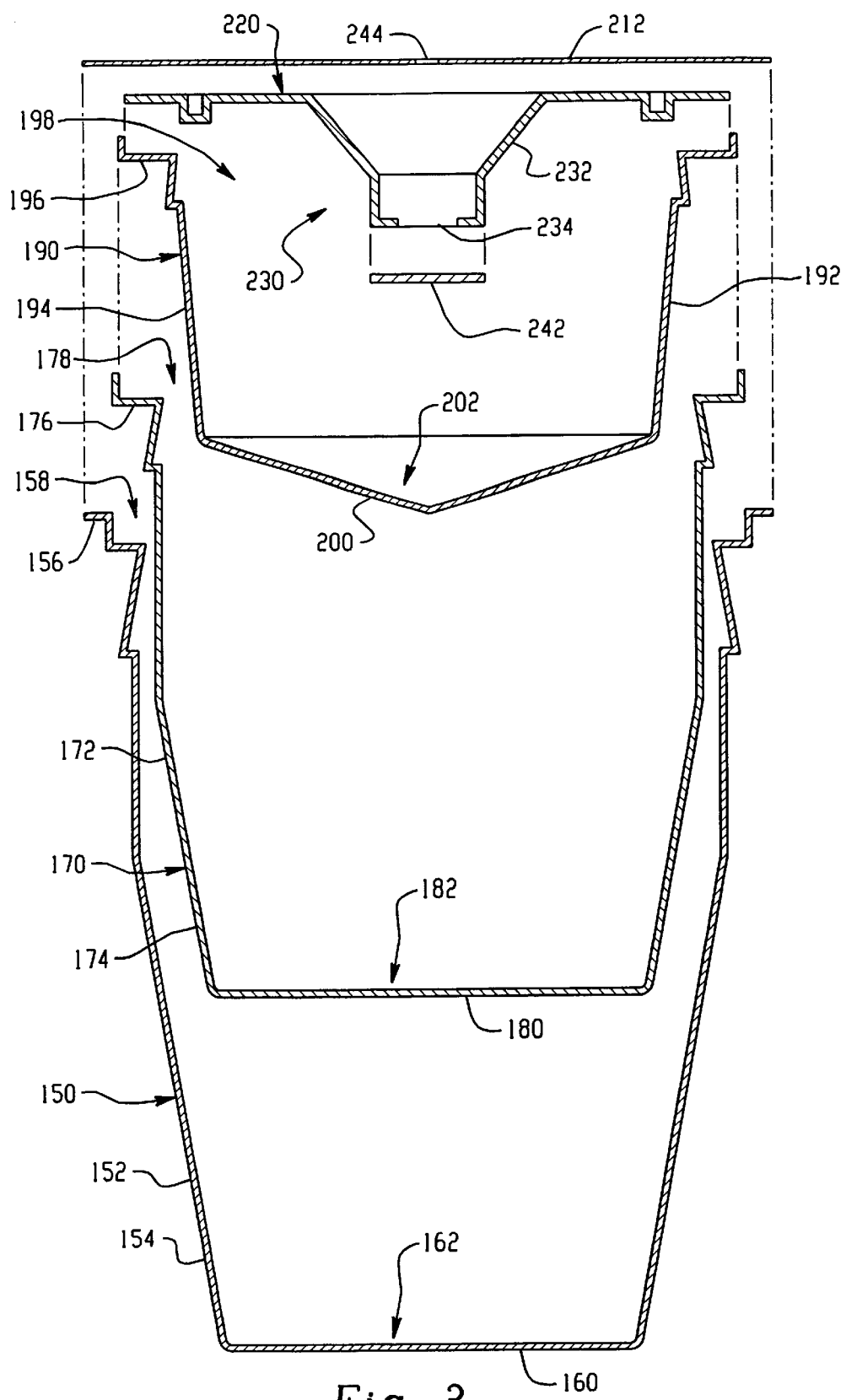
FIG. 3 is an exploded view the three-compartment reagent cartridge of FIG. 2.

With reference to FIGS. 2 and 3, a first preferred embodiment of the multi-compartment cup 44 holds the antimicrobial agent B, preferably a concentrated peracetic acid solution, separate from the composition A, although it is also contemplated that the two portions be mixed together in a single, liquid composition. A cleaner concentrate C is separately contained in the cup 44 for pre-release into the system to remove dirt and other contaminants from the items prior to antimicrobial decontamination.

In another embodiment, only a liquid antimicrobial agent B is contained in a package 44, while the composition A is separately measured and added to the well.

In yet another embodiment, the antimicrobial agent is supplied as reagents which react in water to form the antimicrobial agent in solution. For example, an acetyl donor, such as acetyl salicylic acid, and a perborate, such as sodium metaborate are used to form peracetic acid. These reagents are preferably kept separate until they are to be reacted. For example, one of the reagents is stored in one cup compartment together with the composition A, while the other reagent is separately contained in another compartment.

Alternatively, a solid or liquid antimicrobial agent B is supplied to the system from a separate bulk source (not shown), or is supplied to the system with the composition A as an already-diluted decontaminant solution.

With reference once more to FIGS. 2 and 3, the package 44 includes three compartments for separately holding the cleaner concentrate C, composition A, and antimicrobial agent B. An outer cup 150 is constructed of a light weight, rigid polymeric material and includes a peripheral wall 152. The peripheral wall has a cylindrical side 154 with a flange 156 at a first, open upper end 158 thereof, and a closure, such as an integral base wall 160, which closes a second, opposite end 162 of the side 154. Alternatively the end 162 is closed by a detachable base wall, or by a porous membrane which is impermeable to a solid cleaner concentrate disposed in the outer cup.

A second, or intermediate cup 170 is received in the outer cup 150. The intermediate cup is constructed like the outer cup with a peripheral wall 172 comprising a cylindrical side 174, an integrally molded flange 176, connected with an open, upper end 178 of the cylindrical side, and a closure, such as a base 180, which closes a second, opposite end 182 of the side 174.

A third, or inner cup 190 is received in the intermediate cup 170. The inner cup is constructed like the outer cup with a peripheral wall 192 comprising a cylindrical side 194, an integrally molded flange 196, connected with an open, upper end 198 of the cylindrical side, and a closure, such as a base 200, which closes a second, opposite end 202 of the side 194. The flanges 156, 176, 196 abut and are sealed together by welding, adhesive bonding, or the like.

A first, or outer compartment 208 is defined between the intermediate cup peripheral wall 172 and the outer cup peripheral wall 152. The cleaner concentrate C is inserted into the first compartment prior to welding of the flanges 156,176. Obviously, if the package 44 is not to contain a cleaner concentrate, the outer cup is eliminated.

A second, or intermediate compartment 210 is defined between the inner cup peripheral wall 192 and the intermediate cup peripheral wall 172. The composition A is inserted into the second compartment prior to welding of the flanges 176, 196.

The inner cup 190 is sealed at the top end 198 by a top cover 212. Appropriate sealing methods for the flanges and top cover include heat welding, adhesive bonding, solvent welding, ultrasonic welding, and the like. Together, the inner cup 190 and top cover 212 define an inner, or third compartment 214 for receiving the antimicrobial agent B, such as an aqueous peracetic acid solution at about 30–38% peracetic acid by weight. The third compartment 214 may also contain materials which help to stabilize the antimicrobial agent during storage. The sizing of the compartments is determined by the volumes of the components to be used, and by other factors, which will be discussed further.

Peracetic acid solution and other strong oxidants tend to outgas during storage. Accordingly, an inner cover 220 is positioned between the top cover 212 and the flange 196, to cover the upper end 198. The inner cover includes a venting system 230 for releasing the buildup of gas. The venting system includes a vent passage 232, which is defined in a central region of the inner cover 220. The vent passage extends axially into the third compartment 214. An opening 234 is defined in a distal end of the vent passage. Preferably, the opening is positioned to be at the geometric center of the third compartment 214. The peracetic acid and any other components of the third compartment, occupy less than half of the volume of the third compartment. Thus, irrespective of the orientation of the package 44, the liquid level is always below the opening 234.

To protect against leakage due to splashing, a gas permeable and substantially liquid impermeable membrane 242 is mounted over the opening 234. Gas from the third compartment 214 passes through the membrane 242 and exits the package 44 through a small opening 244 in the top cover 198. The opening may be formed by cutting a slit in the top cover or by using a gas permeable material, such as Tyvek™, for the top cover.

In a typical decontamination cycle, items to be cleaned and microbially decontaminated are first inserted into the cabinet 10 through the door 15, and the door is closed. A fresh cup 44 is inserted into the well 40 and the well closed. The computer control 80 signals the valve 52 in the water inlet line 42 to open, allowing water to circulate through the well and the fluid lines 60 and 66. Once sufficient water has entered the system, the controller 80 closes the valve 52 and signals the opening member 46 to open one or more compartments of the package 44. In the package 44 of FIG. 2, the opening member 46 opens the cleaner compartment 208 of the cup first, for example, by detaching a detachable base or piercing the base 160. The cleaner concentrate C mixes with the water to form a cleaning solution and is delivered by the pump 22 under pressure to the nozzles 16 and endoscope connection ports 18. The nozzles spray the cleaning solution over the outer surfaces of the items while the connection ports deliver the cleaning solution to the internal passages, thereby removing dirt, such as biological materials, pharmaceutical residues, or the like, from inner and outer surfaces simultaneously. Sprayed cleaning solution which drips off the items is collected in the sump 20. The return pump 70 returns the collected solution from the sump to the fluid supply line 60, preferably after first passing a part of the collected solution through the well 40 to ensure complete mixing of the cleaner concentrate C in the solution.

After a period of circulation of the cleaning solution sufficient to remove the bulk of the dirt from the items, a drain valve 250 is opened and the cleaning solution flushed from the system 1 to the drain.

The system 1 is refilled with water, as described above. The controller 80 signals the opener member 46 to open the second compartment 210. Water is forced into the package 44, flushing the composition A from the package. The corrosion inhibitors present coat the system and the surfaces of items to be decontaminated with traces of inhibitors to provide resistance to the corrosive effects of the antimicrobial agent. The buffers present buffer the water in the fluid lines to an appropriate pH for effective decontamination. The opener member 46 then opens the third compartment 214, releasing the antimicrobial agent B into the circulating solution of the composition A, thereby forming a decontaminant solution of the desired concentration. The controller signals the heater 64 to heat the decontaminant solution to the desired temperature. The decontaminant solution is sprayed through the nozzles 16 over the items to be decontaminated. After a period of circulation of the decontaminant solution sufficient to effect decontamination of the items, the drain valve 250 is opened and the decontaminant solution flushed from the system 1 to the drain. The items are then rinsed with water from line 54 to remove traces of the decontaminant solution, minerals, dirt, or other contaminants from the items.

An air line 254 supplies a source of microbe-free air to the system. The air is preferably passed through a microbial filter 256 before entering the system.

After rinsing and drying the items, the items are transferred from the decontamination chamber 12 to sterile pouches and stored until needed. Or, the cabinet 10 is sealed and disconnected and the cabinet and items are transported to a surgery suite or storage facility until needed. In this latter case, a second cabinet, containing used and contaminated items, then replaces the removed cabinet.

While the system 1 has been described with reference to spray nozzles 16, which spray the decontaminant solution over the items within the chamber 12, it should be appreciated that the chamber 12 could alternatively define a receiving tray in which the items are immersed in the decontaminant composition. In this embodiment, the decontaminant solution is flowed over the items such that interior and exterior surfaces of the items are contacted. In yet another alternative embodiment, the composition is combined with an antimicrobial agent in water and the items to be decontaminated are manually immersed in the decontaminant solution.

The antimicrobial agent B is preferably a strong oxidizing agent, such as lithium hypochlorite or peracetic acid. This may be in a liquid form, such as concentrated peracetic acid (preferably obtained as a 30–38 wt % solution in water). Alternatively, dry reagents are used which react in water to form the antimicrobial agent. Preferred dry reagents for forming peracetic acid include an acid precursor, preferably acetylsalicylic acid and a persalt, preferably a perborate, such as sodium perborate. These two reagents are supplied in a sufficient amount to generate a preselected peracetic acid concentration when the composition is diluted with water. The sodium perborate generates hydrogen peroxide, which, in combination with acetylsalicylic acid as an acetyl donor, forms peracetic acid. It is also contemplated using other strong oxidants, such as chlorine, or other reagents which form an antimicrobial agent on mixing with water.

When peracetic acid is used as the antimicrobial agent B, the cup 44 contains sufficient liquid or dry reagents for forming a decontaminant solution of a preselected concentration for decontamination when mixed with water in the system. The concentration of peracetic acid may be as low as about 10–100 ppm for disinfection or as high as from about 1000 ppm–10,000 ppm (1% by weight), for sterilization. A particularly preferred concentration for sterilization is 0.1–0.4% by weight.

The composition A is preferably free of molybdenum (generally molybdates), and is preferably also free of other heavy metals and their compounds which reduce the stability of peracetic acid sterilant or which pose environmental hazards when present in waste waters, such as chromium, cobalt, vanadium, cadmium, mercury, cobalt, tungsten, and the like. In a particularly preferred embodiment, the composition is substantially free of all heavy metals (both elemental metal and compounds thereof), in particular, the transition elements and their compounds. Each of the heavy metals is thus present in no more than impurity amounts, i.e. at no more than about 0.001% by weight of the composition.

The composition A includes a buffering system and corrosion inhibitors, and may also include chelating agents or sequestering agents (both referred to herein generally as chelators). Surfactants may also be present to improve penetration of the decontaminant solution.

In one embodiment, the buffering system in the composition A includes one or more inorganic phosphates, preferably a mixture of phosphates which together buffer the decontaminant solution to an appropriate pH for microbial decontamination (preferably around pH 6–8). The phosphates also provide much of the corrosion inhibition which would conventionally be provided by corrosion inhibitors containing heavy metals, such as molybdates, chromates, vanadates, and tungstates. Accordingly, the phosphates are added in a sufficient amount to provide, in combination with any other heavy metal-free corrosion inhibitors present, a decontaminant solution which does not appreciably corrode parts of devices and decontamination equipment during the decontamination process.

Suitable phosphates for the composition include alkali metal phosphates, such as those of sodium and potassium. Examples of phosphates include monosodium phosphate, disodium phosphate, sodium hexametaphosphate, and potassium equivalents thereof. Preferably, the buffer includes a mixture of two or more phosphates. For example, monosodium phosphate buffers to a relatively acidic, low pH, while disodium phosphate buffers to a basic, higher pH. By combining the two in a selected ratio of mono:disodium phosphate, a selected pH can be obtained. Sodium hexametaphosphate serves as a chelating agent for water hardness salts, and the like, and is therefore useful in the composition.

In another embodiment, the buffering system includes one or more sodium silicates (zeolites) in place of one or all of the phosphates. The zeolites are used in a sufficient amount to buffer the decontaminant solution to a suitable pH for microbial decontamination. Zeolites provide excellent buffering capacity. They also act as surfactants, reducing the surface tension of the decontaminant solution to increase soil removal (such as where an extra cleaning cycle is not used prior to decontamination, or where the cleaning cycle has not removed all of the soil). The reduction in surface tension also enhances penetration of the sterilant into narrow spaces, such as occluded surfaces, lumens, and the like. They also provide a degree of corrosion inhibition, forming a physical barrier to alkali attack on surfaces of the system and the items being decontaminated. This permits the formulation of a composition A which is free of azoles and heavy metal corrosion inhibitors, without a significant effect on corrosion inhibition by the composition. Moreover, the silicates are able to sequester heavy metals in solution, forming heavy metal silicates with reduced solubility, thus performing the functions of the chelator.

The zeolites may be incorporated into the composition in either liquid or solid form. They have the general formula $Na_2O.(SiO_2)_x$, where x is the ratio of silica to alkali and is in the range of 0.4:1 to 4.0:1, preferably in the range 1.60:1 to 3.25:1. Suitable zeolites can be obtained from PQ Corp, Valley Forge, Pa. under the trade names AD40NX and METSO. The zeolite is added to the composition in a sufficient amount to buffer the composition, when diluted with water, to a desired pH for effective decontamination. The zeolite buffer concentration should also be sufficient to compensate for the effects of biological and other materials present on the items being decontaminated. Preferably, the zeolites buffer the pH of the diluted composition to around pH 6–8, more preferably, around pH 7. Preferred compositions A include 10–90% zeolites, more preferably around 20–50%.

Particularly in the case of zeolite buffering systems, the buffering system may also contain other environmentally friendly buffers, such as citric acid or salts thereof.

It has been found by the present inventors that peracetic acid-based decontaminant solutions containing heavy metals and their compounds, such as molybdenum, for example as sodium molybdate, chromium, cobalt, vanadium and also iron, tend to degrade faster (i.e. peracetic acid and its equilibrium components, such as hydrogen peroxide, are converted to compounds which do not provide effective sterilization) than those without the heavy metal. As the solutions without molybdenum (and other heavy metals) retain their peracetic acid activity for longer periods than those with heavy metals present, decontamination can be achieved in a much shorter time or to a higher degree of assurance that microorganisms will be destroyed. The reduction in decontamination time also contributes to a reduction in the corrosion of instruments and equipment. Thus the absence of any beneficial effects of heavy metals in reducing corrosion is compensated for in the present composition by the presence of phosphates, zeolites and/or other corrosion inhibitory compounds and by a reduction in the overall processing time.

Other corrosion inhibitory agents, where desired, are selected in accordance with the nature of the materials in the items being cleaned and/or decontaminated with the decontaminant. Corrosion inhibitors which protect against corrosion of aluminum and steel, including stainless steel, include sulfates and borates. Some additional aluminum corrosion inhibitors include 8-hydroxyquinoline and orthophenylphenol. Preferred copper and brass corrosion inhibitors include azoles, benzoates, other five-membered ring compounds, benzotriazoles, tolyltriazoles, mercaptobenzothiazole, and the like.

One or more organic corrosion inhibitors, in combination with a zeolite or phosphate buffering system provides a good corrosion inhibitor for many of the metals used in the system and the items being decontaminated and allows the composition to be free of heavy metals, such as molybdenum and/or chromium. Additionally, when zeolites are used as the buffering system, both the inorganic and the organic corrosion inhibitors may be reduced or even eliminated.

In hard water, calcium and magnesium salts present tend to precipitate and coat the instruments being decontaminated and/or cleaned and also leave deposits on parts of the system. In such cases, the composition preferably includes one or more chelators (the term "chelator" is used herein to encompass both sequestering agents and chelating agents) appropriate to prevent precipitation or to complex with the metals in these salts. Suitable chelators include ethylene diaminetetraacetic acid (EDTA), and salts thereof, nitrilotriacetic acid, and salts thereof, sodium polyacrylates, and combinations thereof. Of course, if soft or deionized water is utilized, the chelator may be eliminated. However, to ensure universal applicability with any water that might be utilized, the presence of a sequestering agent and/or chelating agent is referred.

The composition preferably contains a total of from about 1 to about 30% by weight of chelators, more preferably, 10–15% by weight of the composition A.

A surface tension reducing agent or wetting agent ("surfactant") is preferably added to the composition to increase penetration into crevices of items being treated. This is particularly important when cleaning and decontaminating complex medical instruments which may contain microbial contaminants in crevices, joints, and lumens. Surface energy reducing agents usable in accordance with the present invention include various wetting agents. Such wetting agents include anionic, cationic, nonionic, amphoteric, and/or zwitterionic surfactants. Specific classes of wetting agents which are useful include anionic and nonionic surfactants or combinations thereof. Examples of nonionic wetting agents usable in the present invention include surfactants such as fatty alcohol polyglycol ethers, nonylphenoxypoly (ethyleneoxy) ethanol, a non-ionic surfactant, and ethoxylated polyoxypropylene, a non-ionic surfactant. Specific examples include Genapol UD-50™, Igepal™ (nonylphenoxypoly (ethyleneoxy) ethanol), Fluowet™, Antarox™ (ethoxylated polyoxypropylene), and Pegol™. The wetting agents set forth above may be used alone or in combination with each other.

The surfactant is preferably present in an amount ranging from about 0.01% to about 8.0% by weight. When zeolites are used as the buffering/chelating system, the surfactant can be at the low end of this range, or even eliminated.

When combined with the antimicrobial agent B and diluted with water, a suitable decontaminant solution is formed. For sterilization, a decontaminant solution is preferably prepared with about 5–8 grams/liter of 35 wt % peracetic acid, and about 10–20 g/l of the composition A (or sufficient for the buffering system in the composition to buffer the decontaminant solution to a pH of about 6–8). The sterilant solution formed thereby is suitable for decontaminating complex-shaped medical devices incorporating a variety of different metals, plastics, and the like, without appreciable corrosion or other damage to the devices or to a decontamination system in which the devices are treated. No significant differences were observed in corrosion measurements over 100 sterilization cycles with the composition A as compared with a composition which was equivalent except in that it contained a molybdate corrosion inhibitor.

Optionally, the composition includes an indicator which changes color in water to indicate that the peracetic acid is present in solution at a minimum selected level or above.

Without intending to limit the scope of the invention, the following examples provide formulations of the composition and the effectiveness of the composition.

EXAMPLES

Example 1

The stability of peracetic acid solutions formed with molybdenum and molybdenum-free compositions was compared. Two formulations were prepared using liquid peracetic acid (about 70 g in 10 liters, to give a nominal initial concentration of 2000 mg/L), to which either composition 1 or composition 2 was added. Composition 1 was molybdenum free. Composition 2 contained sodium molybdate dihydrate. The formulations both included a phosphate buffer system to buffer the decontaminant solution to a suitable pH for decontamination; an organic corrosion inhibitor in an effective amount; a surfactant, a detergent and a chelator in effective amounts for providing penetration of devices to be decontaminated with such compositions. Apart from the sodium molybdate, the compositions were the same.

To make the peracetic acid decontaminant solutions, the composition (1 or 2) was mixed with 10 liters of deionized water at around 50° C. to dissolve the composition. Then, the peracetic acid was added and measurements commenced. The sodium molybdate was at a concentration of about 0.6 g/liter in the decontaminant solution formed from composition 2. The pH of the solution was measured at intervals. Peracetic acid concentrations were also determined at intervals by calorimetric analysis.

Figure 4:
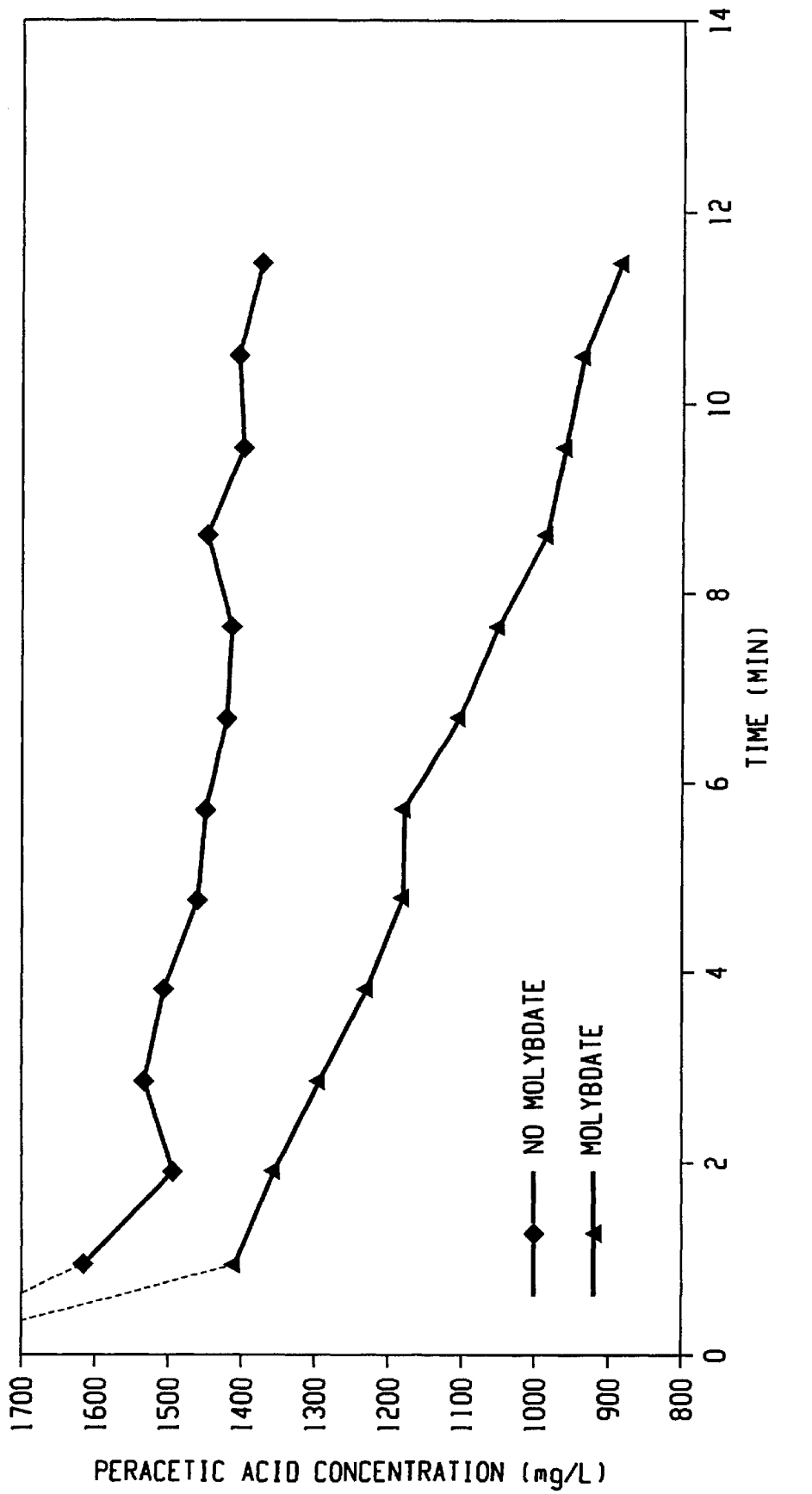
FIG. 4 is a graph of peracetic acid concentration over time for decontaminant solutions with and without molybdates.

With reference to FIG. 4, which shows the peracetic acid concentration over time, the molybdenum-free decontaminant solution ("Moly-free solution") showed significantly better retention of peracetic acid than the molybdenum-containing solution (Moly solution). For example, after 10 minutes, the peracetic acid concentration in the Moly-free solution had dropped from a nominal, initial concentration of about 2000 mg/L to about 1420 mg/L.

In contrast, the Moly solution had dropped to below 900 mg/L. With over 50% more peracetic acid in the Moly-free solution at this time, decontamination can be expected to proceed at a much faster rate than when molybdenum is present.

Figure 5:
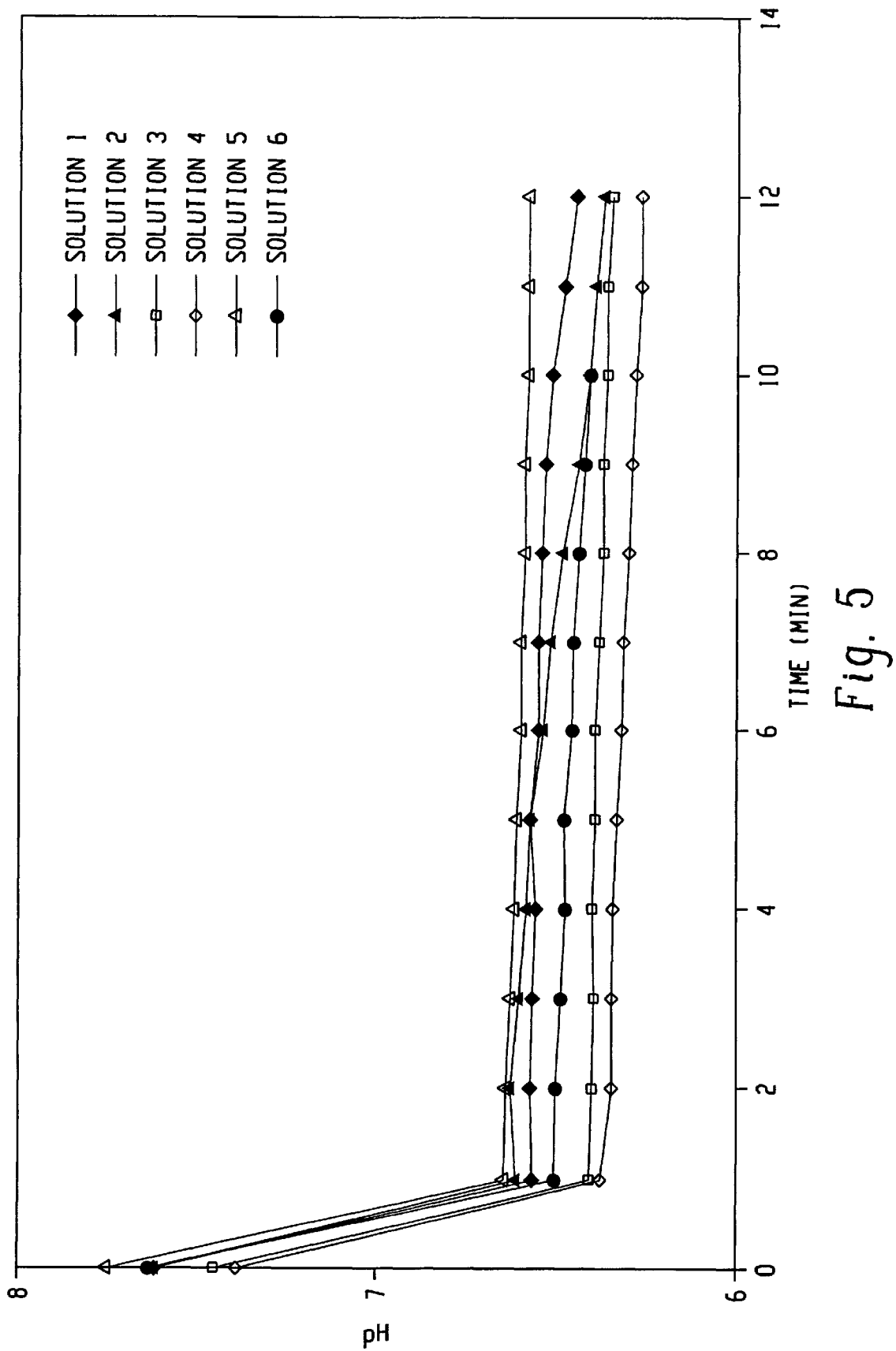
FIG. 5 is a graph of pH over time for solutions without molybdates.
Figure 6:
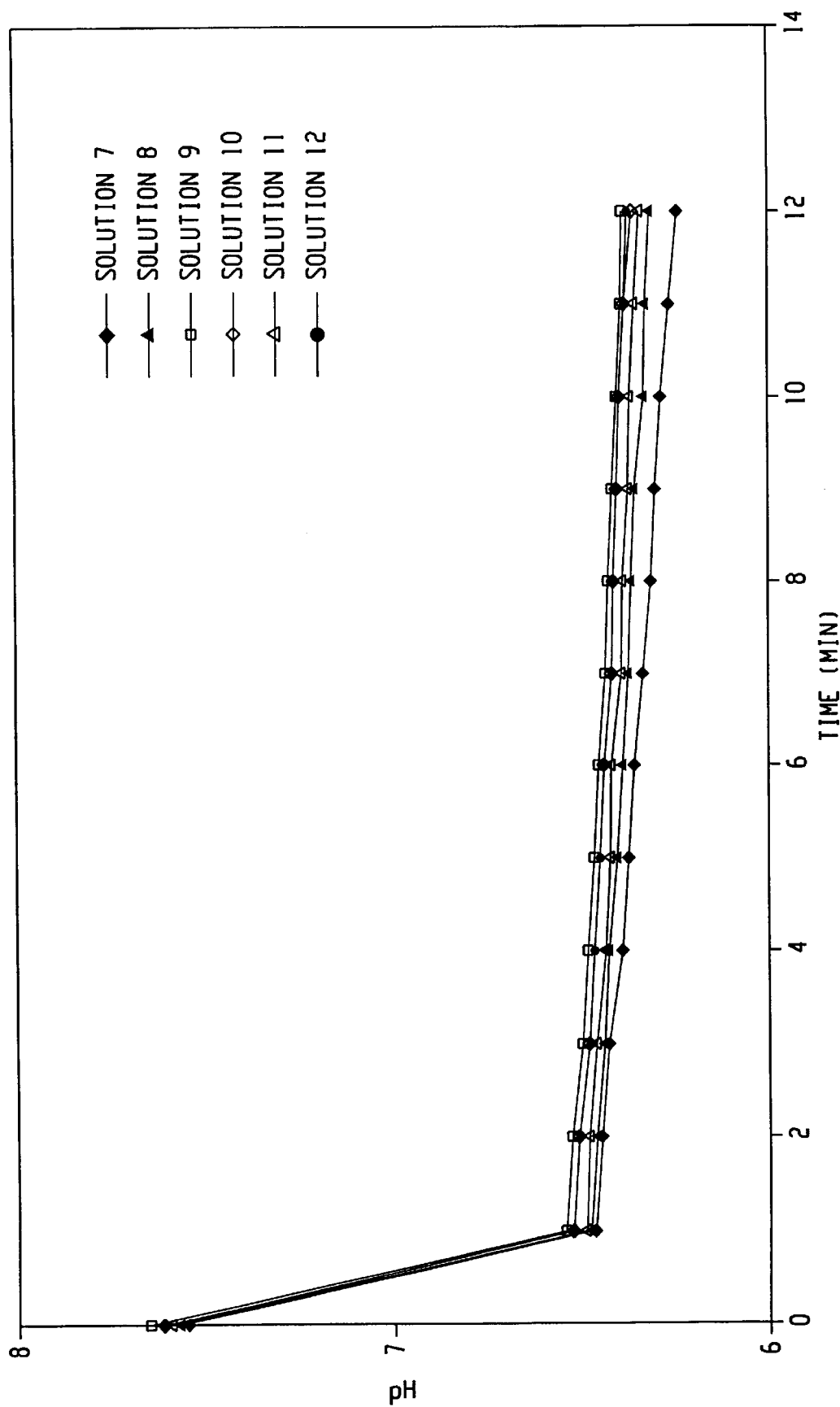
FIG. 6 is a graph of pH over time for solutions with molybdates.

With reference to FIGS. 5 and 6 pH measurements showed relatively similar changes in pH over time with the Moly-free and Moly solutions, respectively. In each case, six, nominally equivalent solutions were prepared and the pH observed over time (solutions 1–6 were Moly-free and solutions 7–12 were Moly). Starting with an initial PH of about 7.5, the pH in both solutions dropped rapidly in the first minute, then stabilized at a pH of about 6.5. Over the following 10–12 minutes, however, the pH of the Moly solution declined steadily to an average of about pH 6.3, whereas the Moly-free solutions declined slightly less, to an average of about pH 6.4.

Experiments carried out in hard water (400 ppm water hardness salts plus heavy metals) or tap water at 40° C., rather than deionized water at 50° C., also showed drops in peracetic acid concentration and pH in the Moly solution.

Example 2

The Moly and Moly-free solutions of Example 1 were tested for their corrosion effects on items typically sterilized. A first set of duodenoscopes were subjected to 100 cycles in a sterilization system with the Moly-free solution (using a fresh solution for each cycle). A second set of duodenoscopes were subjected to 100 cycles in a sterilization system with the Moly solution (using a fresh solution for each cycle). The duodenoscopes were examined for corrosion or other degradation. No significant differences could be detected between the degradation observed on duodenoscopes treated in Moly and Moly-free solutions.

Example 3

Coupons of materials selected to represent items commonly sterilized were exposed to 80 sterilization cycles in either the Moly or Moly-free solutions of Example 1, using a fresh batch of the solution for each cycle. TABLE 1 shows weight changes for the coupons in Moly solutions. TABLE 2 shows the results for coupons in Moly-free solutions. No significant differences were observed between the Moly and Moly-free solutions.

Example 4

A first dry peracetic acid formulation was prepared with conventional phosphate buffers (Composition 3). A second dry peracetic acid formulation was prepared with a zeolite buffer (Composition 4). The two compositions were identical in all respects except for the replacement of phosphate buffers with zeolite buffers in composition 4. Both formulations contained sodium perborate, in a first cup (together with the composition A, comprising buffers, corrosion inhibitors, and surfactants) and acetyl salicylic acid in a second cup. Both compositions were free of molybdates and other heavy metals and their compounds. An organic corrosion inhibitor, a chelating agent, and a surfactant formed part of the composition A in each of Compositions 3 and 4. TABLE 3 shows the formulations of each of the compositions 3 and 4.

In each case, when the contents of the two cups were mixed with water, the acetyl salicylic acid and sodium perborate reacted to form peracetic acid at an initial concentration of about 1800–2000 ppm. Composition 4 was formulated at three different levels of zeolite: 1%, 6%, and 15% by weight of the total weight of the outer cup components.

TABLE 3

| Component of Formulation | Purpose in Formulation | Composition 3 (g/100 mL) | Composition 4 (g/100 mL) |
|---|---|---|---|
| Outer Cup Components | | | |
| Sodium perborate monohydrate | Activator | 1.90 | 1.90 |
| Phosphates | Phosphate buffer system Buffer, anti-corrosive, sequestering | 0.49 | 0.00 |
| Zeolites | Buffer, anti-corrosive | 0.00 | 1%, 6%, or 15% by weight of total outer cup components |
| Other components of composition A, including surfactants, chelators, and corrosion inhibitors | Detergent surfactant, sequestering, chelating agents, anticorrosive | 0.19 | 0.19 |
| Total outer cup components | | 2.58 | |
| Inner cup components | | | |
| Acetyl-salicylic acid | Activator | 0.96 | 0.96 |
| Other components | Stabilizers sequestrants, etc. | 0.82 | 0.91 |
| Total formulation | | 4.37 | |

The inner cup and outer cup components were mixed together with 100 mL of tap water to form a sterilant solution. The pH of the solution was measured at intervals. Hydrogen peroxide concentration and peracetic acid concentration were also determined at intervals.

Figure 7:
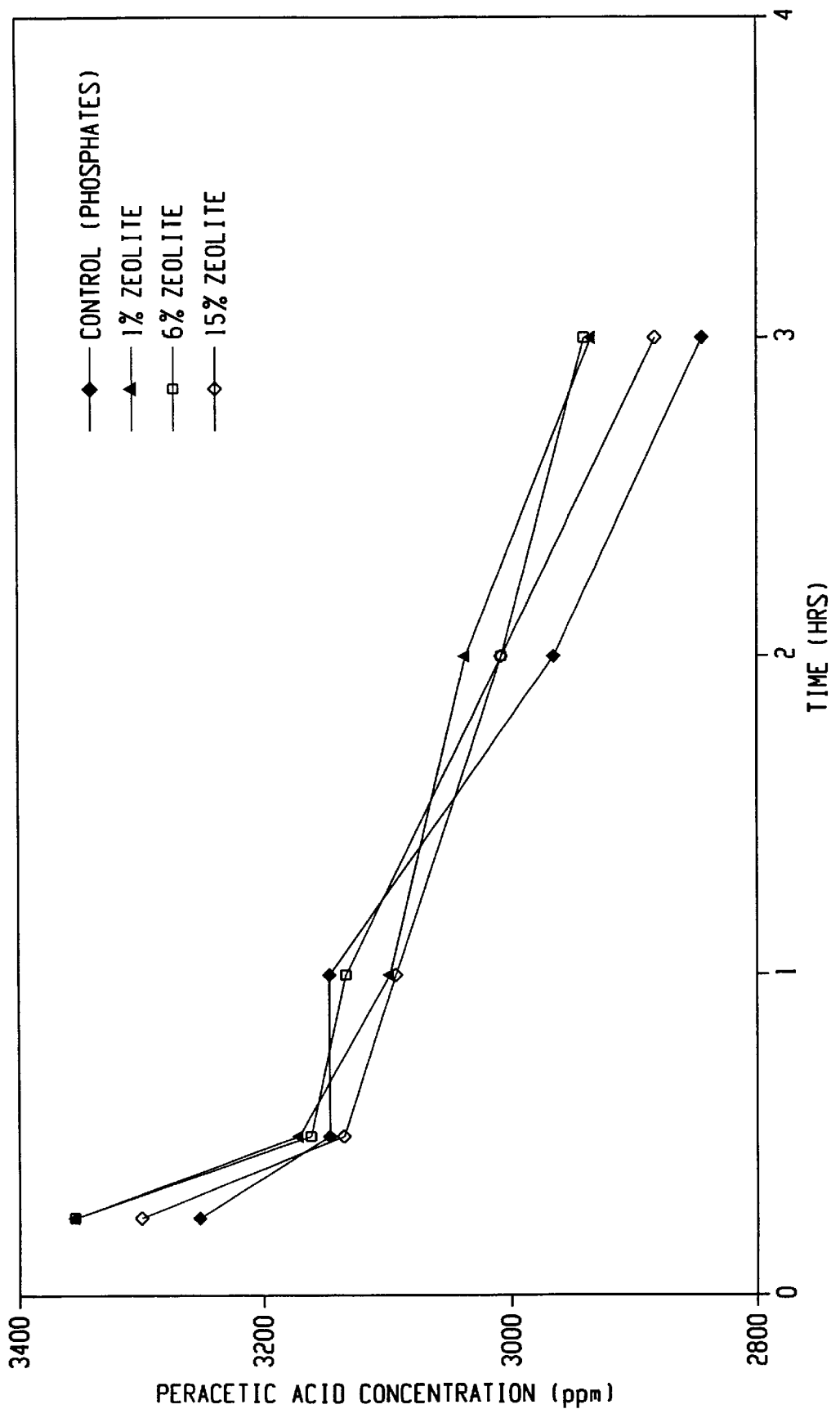
FIG. 7 is a plot of peracetic acid concentration over a three hour period for decontaminant solutions containing various concentrations of zeolites (composition 4), or a phosphate buffer (composition 3—"control")

With reference to FIG. 7, the zeolite compositions at 1, 6, and 15% showed good retention of peracetic acid concentration, over a three hour period, when compared to composition 3 using a phosphate buffer system (labelled "control").

Figure 8:
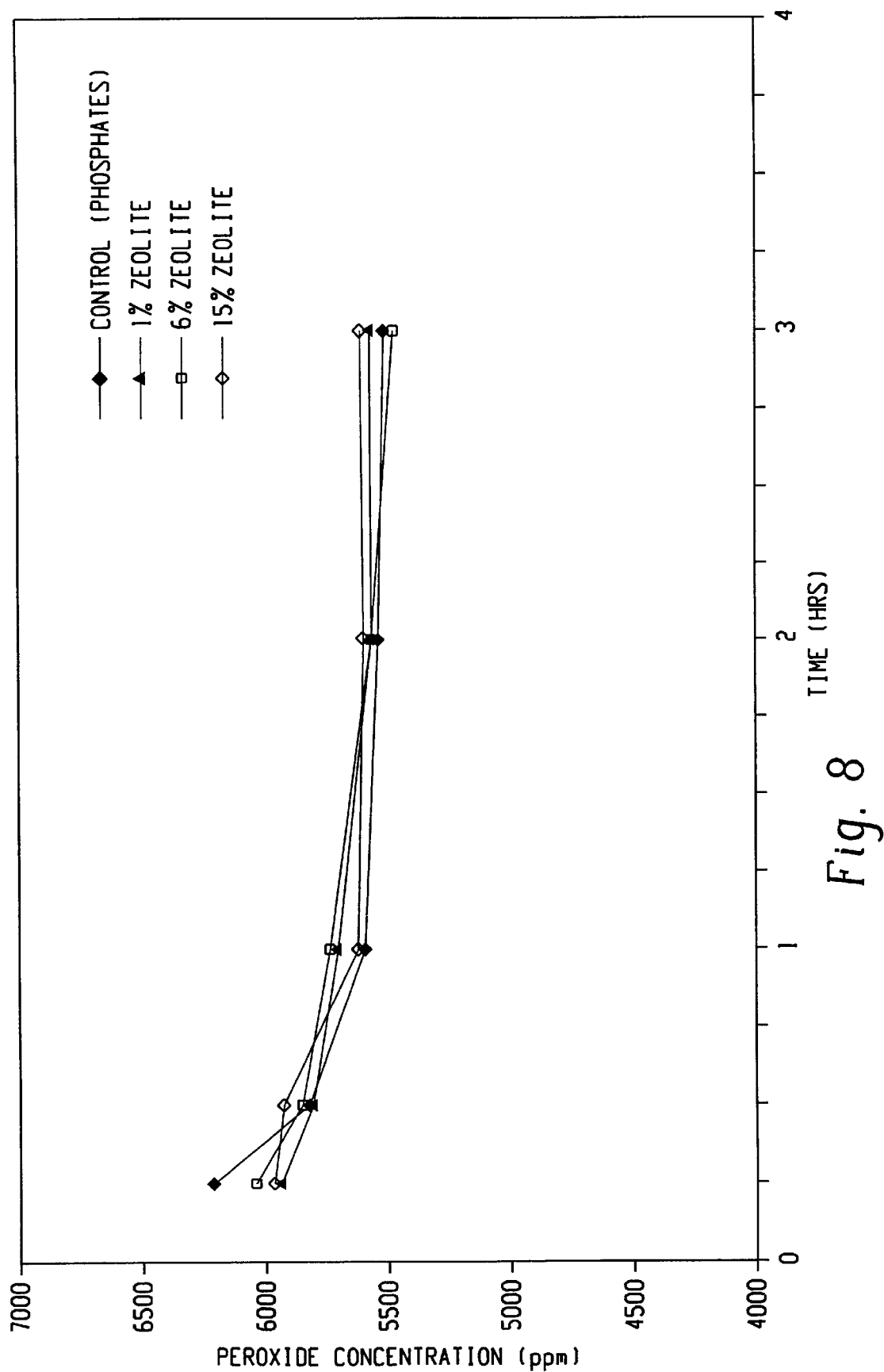
FIG. 8 is a plot of peroxide concentration over a three hour period for decontaminant solutions containing various concentrations of zeolites (composition 4), or a phosphate buffer (composition 3).

With reference to FIG. 8, hydrogen peroxide concentrations for the zeolite (composition 4) over a three hour period were similar to those obtained with a phosphate based system (Composition 3).

The results show the effectiveness of the buffer system over a wide range of zeolite concentrations.

Example 5

Phosphate-buffered and zeolite-buffered compositions were made as for Example 4 and mixed with 100 mL tap water. In the zeolite composition (composition 4), 0.021 g of zeolite was used. After stirring each composition in a beaker for 30 minutes, the following test coupons were added to the respective beakers: a brass coupon, a stainless steel coupon, and an aluminum coupon. No color change was observed in any of the solutions over a twelve hour observation period, indicating an absence of corrosion in each case.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

TABLE 1

MATERIAL COMPATIBILITY TESTING RESULTS
Mass Readings of Coupons Tested with Molybdate

| Coupon | | Mass at 0 cycles (grams) | Mass at 80 cycles (grams) | wt. change (g) | Average of 3 |
|---|---|---|---|---|---|
| PVC | sample 1 | 7.7490 | 7.7499 | +0.0009 | +0.0009 |
| PVC | sample 2 | 7.7180 | 7.7190 | +0.0010 | |
| PVC | sample 3 | 7.8510 | 7.8519 | +0.0009 | |
| Stainless Steel 304 | sample 1 | 13.5680 | 13.5679 | −0.0001 | −0.0002 |
| Stainless Steel 304 | sample 2 | 11.3466 | 11.3464 | −0.0002 | |
| Stainless Steel 304 | sample 3 | 11.3487 | 11.3485 | −0.0002 | |
| Brass | sample 1 | 24.1391 | 24.1390 | −0.0001 | −0.0004 |
| Brass | sample 2 | 24.1126 | 24.1118 | −0.0008 | |
| Brass | sample 3 | 24.1073 | 24.1070 | −0.0003 | |
| Polyurethane | sample 1 | 0.3221 | 0.3215 | −0.0006 | −0.0007 |
| Polyurethane | sample 2 | 0.3904 | 0.3895 | −0.0009 | |
| Polyurethane | sample 3 | 0.3534 | 0.3528 | −0.0006 | |
| Anodized Aluminum | sample 1 | 7.7529 | 7.7486 | −0.0043 | −0.0035 |
| Anodized Aluminum | sample 2 | 7.7823 | 7.7783 | −0.0040 | |
| Anodized Aluminum | sample 3 | 7.7553 | 7.7531 | −0.0022 | |
| Stainless Steel 316L | sample 1 | 22.6380 | 22.6377 | −0.0003 | −0.0002 |
| Stainless Steel 316L | sample 2 | 22.4663 | 22.4661 | −0.0002 | |
| Stainless Steel 316L | sample 3 | 22.5530 | 22.5529 | −0.0001 | |
| Aluminum | sample 1 | 7.7209 | 7.7197 | −0.0012 | −0.0010 |
| Aluminum | sample 2 | 7.7549 | 7.7544 | −0.0005 | |
| Aluminum | sample 3 | 7.8207 | 7.8194 | −0.0013 | |

TABLE 2

MATERIAL COMPATIBILITY TESTING RESULTS
Mass Readings of Coupons Tested without Molybdate

| Coupon | | Mass at 0 cycles (grams) | Mass at 80 cycles (grams) | wt. change (g) | Average of 3 |
|---|---|---|---|---|---|
| PVC | sample 1 | 7.6811 | 7.6825 | +0.0014 | +0.0014 |
| PVC | sample 2 | 8.1368 | 8.1382 | +0.0014 | |
| PVC | sample 3 | 7.9083 | 7.9096 | +0.0013 | |
| Stainless Steel 304 | sample 1 | 13.5942 | 13.5942 | 0 | +0.0001 |
| Stainless Steel 304 | sample 2 | 13.7170 | 13.7170 | 0 | |
| Stainless Steel 304 | sample 3 | 13.4462 | 13.4465 | +0.0003 | |
| Brass | sample 1 | 24.1285 | 24.1282 | −0.0003 | −0.0005 |
| Brass | sample 2 | 24.0830 | 24.0826 | −0.0004 | |
| Brass | sample 3 | 24.1129 | 24.1120 | −0.0009 | |
| Polyurethane | sample 1 | 0.3961 | 0.3973 | +0.0012 | +0.0001 |
| Polyurethane | sample 2 | 0.3467 | 0.3464 | −0.0003 | |
| Polyurethane | sample 3 | 0.3336 | 0.3330 | −0.0006 | |
| Anodized Aluminum | sample 1 | 7.7624 | 7.7598 | −0.0026 | −0.0036 |
| Anodized Aluminum | sample 2 | 7.7567 | 7.7520 | −0.0047 | |
| Anodized Aluminum | sample 3 | 7.7614 | 7.7580 | −0.0034 | |
| Stainless Steel 316L | sample 1 | 22.4666 | 22.4664 | −0.0002 | −0.0001 |
| Stainless Steel 316L | sample 2 | 22.5367 | 22.5367 | 0 | |
| Stainless Steel 316L | sample 3 | 22.3254 | 22.3253 | −0.0001 | |
| Aluminum | sample 1 | 7.7150 | 7.7139 | −0.0011 | −0.0010 |
| Aluminum | sample 2 | 7.7703 | 7.7697 | −0.0006 | |
| Aluminum | sample 3 | 7.7768 | 7.7756 | −0.0012 | |

Having thus described the preferred embodiment, the invention is now claimed to be:

1. A method of decontamination of medical instruments comprising:

combining an antimicrobial agent and a composition with water to form a decontaminant solution, the composition including:
a buffering system for buffering the pH of the decontaminant solution to a suitable pH for antimicrobial decontamination, the buffering system including at least one zeolite, the composition being free of molybdenum; and contacting the medical instruments to be decontaminated with the solution for sufficient time to substantially antimicrobially decontaminate them.

2. The method of claim 1, wherein the antimicrobial agent includes peracetic acid and the method further includes:
forming the peracetic acid from an acetyl donor and a perborate.

3. The method of decontamination of claim 1, wherein the zeolite is of the general formula $Na_2O \cdot (SiO_2)_x$, where x is the ratio of silica to alkali and is in the range of 0.4:1 to 4.0:1;

and further including:
a corrosion inhibitor for inhibiting corrosion of metal components to be contacted by the decontaminant solution.

4. The method of claim 3, wherein x is in the range of 1.60:1 to 3.25:1.

5. A method of decontamination of a medical, dental, or pharmaceutical device comprising:

releasing a cleaner concentrate for cleaning the device from a first compartment of a package;
forming a cleaning solution from the cleaner concentrate;
cleaning the device with the cleaning solution;
releasing a composition from a second compartment of the package;
forming a solution with the composition and water;
releasing one of an oxidizing agent and a reagent for forming the oxidizing agent from a third compartment of the package;
combining the oxidizing agent with the solution formed from the composition to form a decontaminant solution; and
decontaminating the device with the decontaminant solution;

the composition including:
a buffering system which buffers the pH of the decontaminant solution including at least one buffer selected from the group consisting of phosphates and zeolites, and
an organic corrosion inhibitor for inhibiting corrosion of metal components to be contacted by the decontaminant solution, the composition and the decontaminant solution being free of molybdenum.

6. The method of claim 5, wherein the oxidizing agent includes peracetic acid.

7. The method of claim 6, wherein the method further includes:
forming the peracetic acid from an acetyl donor and a perborate, one of the acetyl donor and a perborate being released from the second compartment and the other of the acetyl donor and a perborate being released from the third compartment.

8. The method of claim 5, wherein the buffering system includes phosphates.

9. The method of claim 5, wherein the decontaminant solution is free of heavy metals, the buffering system includes a zeolite, the zeolite being present at a concentration of from 10–90% of the composition, the composition being free of phosphates.

10. The method of claim 5, wherein the decontaminant solution is free of heavy metals.

11. The method of claim 5, wherein the composition further includes a surfactant at a concentration of 0.01–8% by weight of the composition.

12. The method of claim 5, wherein the composition further includes a chelator at a concentration of from 1–30% by weight of the composition.

13. A method of decontaminating a medical, dental, or pharmaceutical device comprising:

cleaning the device with a cleaning solution to reduce biological load;

combining peracetic acid and a composition with water to form a decontaminant solution, the composition including:
- an organic corrosion inhibitor,
- a buffering system for buffering the pH of the decontaminant solution to a pH of 6–8, the buffering system including at least one zeolite, and
- the composition being free of molybdenum; and contacting the device to be decontaminated with the decontaminant solution for sufficient time to biologically decontaminate the device, the decontaminant solution being free of molybdenum or other heavy metals which accelerate decomposition of the peracetic acid and result in incomplete biological decontamination or an increased decontamination time.

14. The method of claim 13, wherein the method further includes:

forming the peracetic acid from an acetyl donor and a perborate.

15. The method of claim 13, wherein during the step of contacting the device, the decontaminant solution has a peracetic acid concentration of from 1000 to 2000 ppm.

* * * * *